United States Patent [19]
Ito et al.

[11] Patent Number: 5,688,683
[45] Date of Patent: *Nov. 18, 1997

[54] PLASMID PBUL1 DERIVED FROM A LACTOBACILLUS AND DERIVATIVES THEREOF

[75] Inventors: Yoshiyuki Ito; Yasuko Sasaki; Takashi Sasaki, all of Kanagawa-ken, Japan

[73] Assignee: Meiji Milk Products Company Limited, Tokyo, Japan

[*] Notice: The term of this patent shall not extend beyond the expiration date of Pat. No. 5,426,047.

[21] Appl. No.: 396,126

[22] Filed: Feb. 28, 1995

Related U.S. Application Data

[63] Continuation of Ser. No. 940,852, filed as PCT/JP92/00193 Feb. 24, 1992, Pat. No. 5,426,047.

[30] Foreign Application Priority Data

| Feb. 22, 1991 | [JP] | Japan | 3-112674 |
| Mar. 28, 1991 | [JP] | Japan | 3-87338 |
| Jun. 28, 1991 | [JP] | Japan | 3-183922 |

[51] Int. Cl.$^6$ .................................................. C12N 1/21
[52] U.S. Cl. ........................ 435/252.3; 435/252.9
[58] Field of Search .......................... 435/252.3, 252.9

[56] References Cited

U.S. PATENT DOCUMENTS 5,426,047  6/1995  Ito et al. .................. 435/252.3

FOREIGN PATENT DOCUMENTS 0319690  6/1989  European Pat. Off. .
3251172  11/1991  Japan .

OTHER PUBLICATIONS

Todd R. Klaenhammer, "A General Method for Plasmid Isolation in Lactobacilli", *Current Microbiology*, vol. 10, 1984, pp. 23–28.

Vescovo et al., "Evidence of Plasmid Deoxyribonucleic Acid in Lactobacillus", *Microbologica* (Bologna), vol. 4, No. 4, 1981, pp. 413–420.

Miteva et al., "Isolation and Characterization of Plasmids from Different Strains of *Lactobacillus bulgaricus* Lactobacillus . . . ", *Acta Microbiologica Bulgarica*, vol. 27, No. 0, 1991, pp. 3–8.

Holo et al., "High–Frequency Transformation by Electroporation, of Lactococcus . . . ", *Applied and Environmental Microbiology*, vol. 55, No. 12, Dec. 1989, pp. 3119–3123.

Mercenier et al., "Molecular Genetics of Streptococcus Thermophilus", *Fems Microbiology Review*, vol. 87, 1990, pp. 61–78.

Scheirlinck, T., "Integration and Expression of α–Amylase and Endogulcanase Gens in the Lactobacillus . . . ", *Applied and Environmental Microbiology*, vol. 55, No. 9, Sep. 1989, pp. 2130–2137.

Chassey et al., "Transformation of *Lactobacillus casei* by Electroporation", *Fems Microbiology Letters*, vol. 44, 1987, pp. 173–177.

Willem De Vos, "Gene Cloning and Expression in Lactic streptococci", *Fems Microbiology Letters*, vol. 46, No. 1987, pp. 281–295.

Jan Kok, "Construction of Plasmid Cloning Vectors for Lactic streptococci which Also . . . ", *Appl;ied and Environmental Microbiology*, vol. 48, No. 4, Oct. 1984, pp. 726–731.

Simon et al., "Construction of a Vector Plasmid Family and its Use for Molecular Cloning in *Streptococcus lactis*", *Biochimie*, vol. 70, 1988, p. 559–566.

(List continued on next page.)

*Primary Examiner*—Nancy Degen
*Attorney, Agent, or Firm*—Browdy and Neimark

[57] ABSTRACT

Disclosed is the plasmid pBUL1 having a restriction endonuclease cleavage map as shown in FIG. 1 and having a length of about 7.9 kbp and its derivatives. The plasmid was isolated from *Lactobacillus delbrueckii* subsp. bulgaricus M-878. The plasmid is useful as a vector for breeding various microorganisms such as lactic acid bacteria, and the derivatives thereof are useful also as a shuttle vector.

16 Claims, 8 Drawing Sheets

OTHER PUBLICATIONS

Efthymiou et al., "An Antigenic Analysis of *Lactobacillus acidophilus*", *University of Maryland Department of Microbiology*, Dec. 18, 1961, pp. 258–267.

LeBlanc et al., "Physical and Genetic Analyses of Streptococcal Plasmid pAMB1 and Cloning of Its Replication Region", *Journal of Bacteriology*, vol. 157, No. 2, Feb. 1984, pp. 445–453.

Chang et al., "High Frequency Transformation of *Bacillus subtilis* Protoplasts by Plasmid DNA", *Molecular Genetics*, vol. 168, 1979, pp. 111–115.

Yamane et al., "Changes in the Properties and Molecular Weights of *Bacillus subtilis* M–type and N–type α–Amylase Resulting . . . ", *J. Biochem.*, vol. 96, 1984, pp. 1849–1858.

Ando et al., "Kosoh–kin (*Bacillus subtilis*)", *Lectures on Fundamental Microbiology*, 1987, pp. 168–215.

Sambrook et al. *Molecular Cloning: A Laboratory Manual*, (Cold Spring Harbor Laboratory), Cold Cold Spring Harbor, N.Y. pp. 1.12–1.20, 1989.

Somkuti et al., "General Method for Plasmid DNA isolation from Thermophilic Lactic Acid Bacteria", *Journal of Biotechnology*, vol. 3, pp. 323–332, 1986.

Langella et al., "Conjugal Transfer to Plasmid pIP501 from *Lactococcus lactis* to . . . ", *Fems Microbiology Letters*, vol. 60, pp. 149–152, 1989.

Ohiaguchi et al., *J. Chem. Eng. Japan*, 20(6), (1987), pp. 557–562.

Anderson et al., "Simple and Rapid Method for Isolating Large Plasmid DNA from Lactic . . . ", *Applied and Environmental Microbiology*, vol. 46, No. 3, Sep. 1983, pp. 549–552.

Ohtaguchi et al. (1987), J. Chem. Eng. Japan 20(6): 557–562.

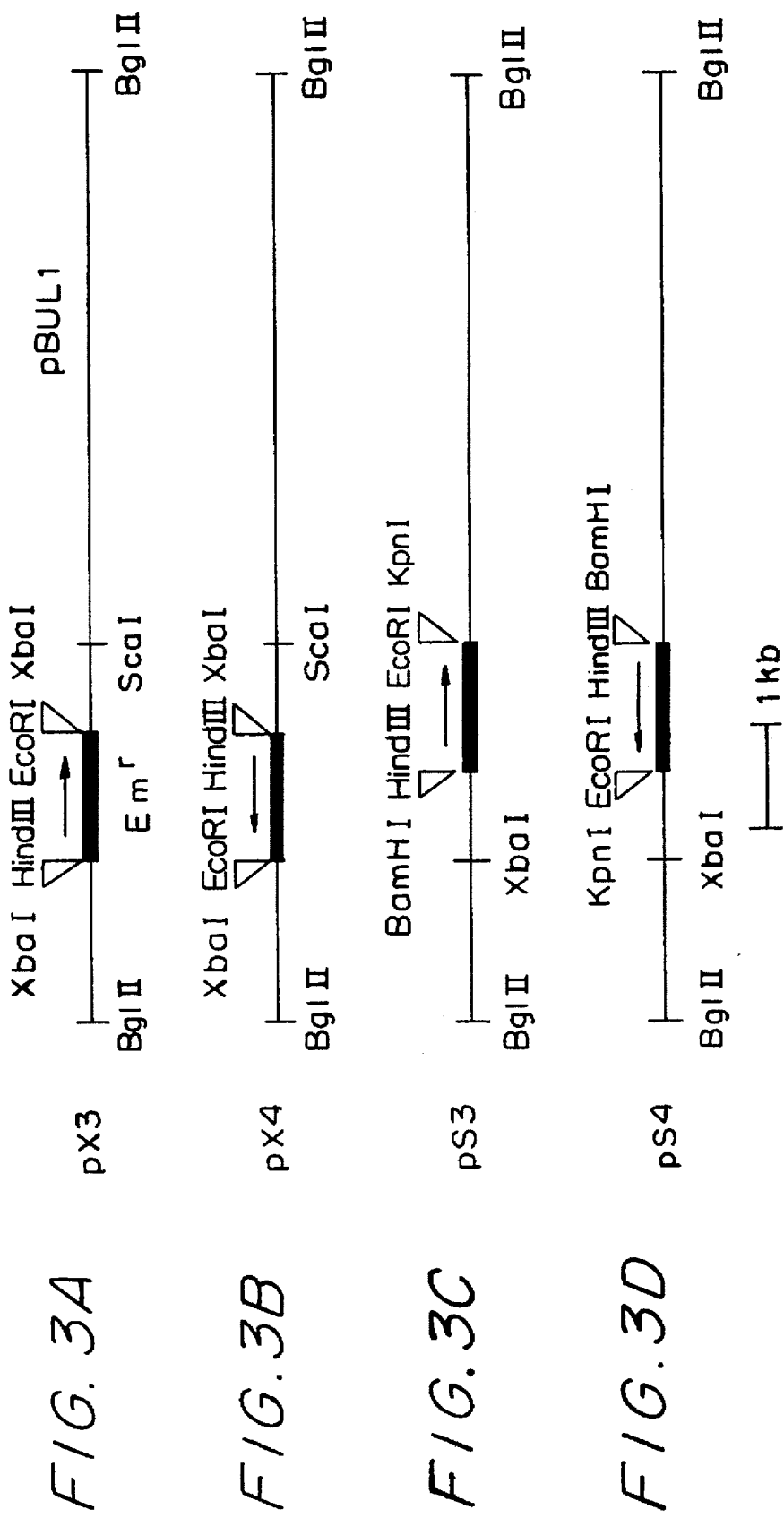

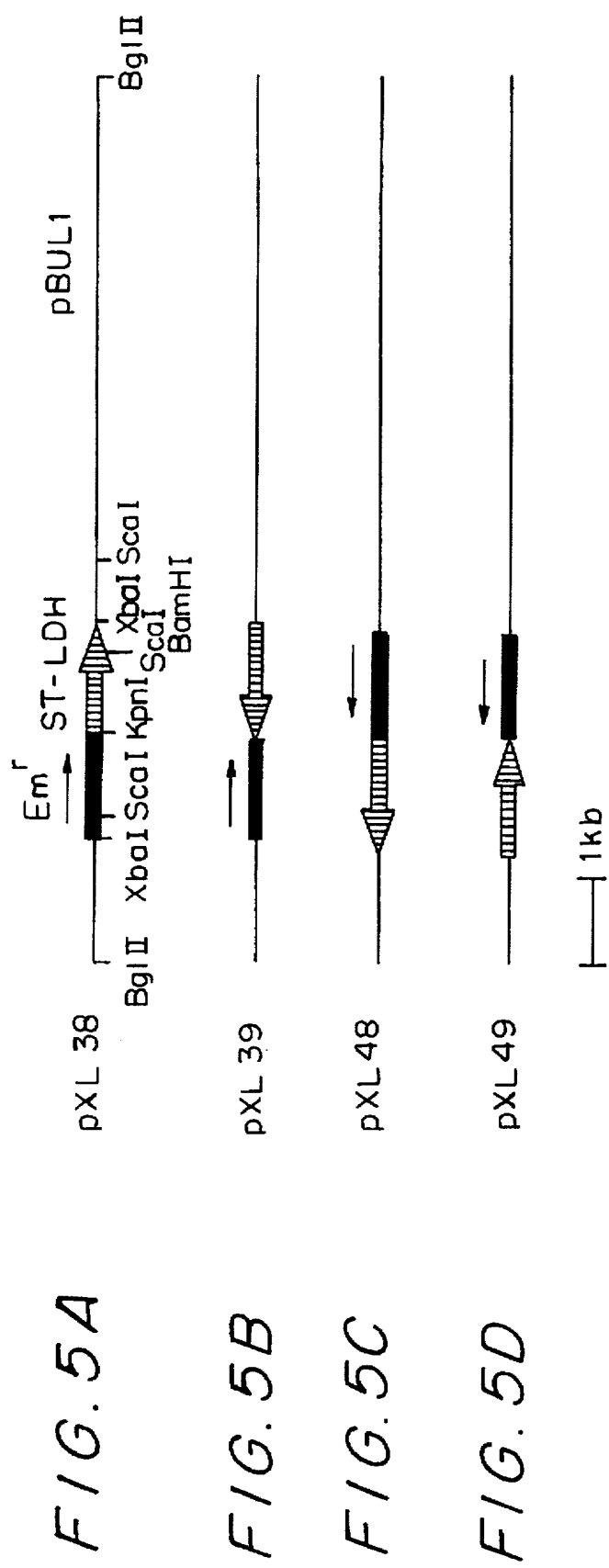

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
   ( A ) LENGTH: 1344 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:1:

CCCGGGGCGA AACGACATGG GGCGCTCAAA CCATTGCTGA GGCGATCAAT TACGTGCAAG    60

| | | | | | | |
|---|---|---|---|---|---|---|
| CCCAGCATCC | CGATCACGGC | TATTTCCCAG | CTCGCCAAAA | TTCCGGCATG | AGGGTTGTTG | 120 |
| AACCGGGTGA | AAGAGCCACA | GGCGAAACGC | TTAGAATTAC | GATTGACGGA | CAGGAAAGAG | 180 |
| AATTTCCGTT | CAACGGCTTT | TTCTATAACC | GGGATTATGA | AATGACCGAG | GTTGGGTTTG | 240 |
| CTAACAGGTT | TGCCGATTGG | TACGCCAAAG | GGAAACTTGT | TTATCACCCC | GGCTTAAAGG | 300 |
| CGTGGCTTAT | GTACAACCCA | GAAACGGGGT | CATGGATGCC | GAATGAAGAC | GACAGACTGG | 360 |
| GCAAGGATTT | TAACCAGACC | CCGGAAAAAC | TCATCGATAA | CTTGCGGATA | AACCTCAAAT | 420 |
| TTGAACAACC | GCTATGGAAA | AAAGTTGGGT | TTAATCCCCA | AAAGCCTAAT | AATCAAACAT | 480 |
| TCGGGGAAAA | GGCTTATGCT | AGTGGCTATA | GCCGGATCAG | CACGGCCGCT | GGGCAAAAGG | 540 |
| CGACCCTTGA | ATTAGCTCAG | AGCCGTTTAA | CCGTGCGTGC | ATTAACGAC | TGTAAGACCG | 600 |
| AGCTTAACAC | CCAGACAGGT | TGGATTGACC | TCAAACGGG | TGCTATTAGC | CCTCACAACC | 660 |
| CGGCGAAACT | TTTTGACAAG | GTCACGGATG | CTGGTTTGCC | TAATAAAGCC | ACAGAGGGTG | 720 |
| ATGGCGGCAA | GCTCTGGGAT | CGTTTCCTGA | AAGAGACCTT | TTGCGGCGAT | CTTGATTTGA | 780 |
| TCGAGTTCGT | ACAGGCCTGC | ATAGGCTACA | GCATTACGGG | CAAAATCAAT | GAACAGGTCA | 840 |
| TGTTTATCTG | CAAAGGCAGT | GGGGGCAACG | GGAAGAGCAT | TTTTCTTGAA | TGCTTAAACG | 900 |
| AGGTGCTGGG | CGATTATAGC | TCTGTTATCC | CAATAGAAAC | GCTAACAGAC | AACGGCAAGG | 960 |
| CTCAGCGTGA | CGGATCAGCA | CCAAGTCCAG | ACCTTGCAAG | CCTTGAGGGC | AAGCGGTTCG | 1020 |
| TTATTACGAG | CGAACCGAAA | GAGCAGGTTA | CAATCGATGC | TGGGACGGTC | AAAACGGTGA | 1080 |
| CGGGTGGCAC | TAAGTTAAAA | GTTAGAATGC | TACACCAAAA | CCCGATTGAG | TTCCTGCCAC | 1140 |
| AGTTTAAAAT | TTGGTGGCAA | TCTAACGGCT | TGCCAAACGT | CAACTTTAAC | GATTATGCTA | 1200 |
| TTTTACGGCG | CTTGATCGTC | ATCCCGTTTA | AAAATGAGGT | GCGAGAGGAT | GCGGTAGATA | 1260 |
| TCAACCTCAA | AAGCAAGCTA | ATGAAAGAGA | AAGAGTTTAT | TTTAAAGTGG | TGTGTTGAGG | 1320 |
| GCGTGGCTAA | ATGGCAAGCC | CGGG | | | | 1344 |

PLASMID PBUL1 DERIVED FROM A LACTOBACILLUS AND DERIVATIVES THEREOF

This is a continuation of parent application Ser. No. 07/940,852 filed Oct. 22, 1992 filed as PCT/JP92/00193 Feb. 24, 1992 now U.S. Pat. No. 5,426,049.

FIELD OF THE INVENTION

The present invention relates to a novel circular double-stranded DNA plasmid pBUL1 derived from *Lactobacillus delbrueckii* subsp. bulgaricus, the utility and safety of which as a yogurt-producing bacterium are well known, and to derivatives thereof, as well as to microorganisms transformed with the plasmids.

PRIOR ART AND PROBLEMS TO BE SOLVED BY THE INVENTION

Lactic acid bacteria are very useful microorganisms which have long been used in production of various fermented foods. If a recombinant DNA technology which has rapidly been developed in recent years could be applied to lactic acid bacteria, greater enhancement of the utility of the bacteria would be expected. In fact, host-vector systems with a fairly high efficiency have already been reported for lactic acid bacteria of some species of, for example, *Lactococcus lactis* (reference 1), *Streptococcus salivarius* subsp. thermophilus (reference 2), *Lactobacillus plantatum* (reference 3) and *Lactobacillus casei* (reference 4), and the current stage of the technical improvement is use the host-vector systems on an industrial scale.

However, despite great efforts by many researchers, there has hitherto been no report of transformation of *Lactobacillus delbrueckii* subsp. bulgaricus and *Lactobacillus delbrueckii* subsp. lactis (hereinafter referred to as *Lb. bulgaricus*, and *Lb. lactis*, respectively), which are used extensively as bacteria for producing milk products such as yogurt. Application of broad-host-range plasmids, such as pNZ12 (reference 5), pGK12 (reference 6) and pIL253 (reference 7) with which transformants of lactic acid bacteria of some species have been obtained, to the above-mentioned two subspecies has been attempted, but transformation was not successful. However, establishment of host-vector systems of the above-mentioned two subspecies has been earnestly desired;

If a recombinant DNA technology is applied to microorganisms to be used in production of foods, the safety of vectors to be used for transformation of them must be established. As vectors, for this purpose those vectors are desirable which exist naturally in microorganisms that have been used to produce foods which have traditionally been eaten and the safety of which has been historically confirmed. On the other hand, fermented milk products such as yogurt are foods which have been eaten for a long period of time and their safety has been well confirmed. Therefore, the plasmids derived from microorganisms from fermented milk products, for example, those of the above-mentioned two subspecies, are useful vectors in order to construct transformants of microorganims for food production. In addition they are also available vectors for transformation for the purpose of producing various physiologically active substances.

Means for Solving the Problems

For the purpose of developing host-vector systems for *Lb. bulgaricus* and *Lb. lactis*, the present inventors variously investigated and studied plasmids of these subspecies. As a result, they are the first who have succeeded in isolating a plasmid from *Lb. bulgaricus* M-878 strain (FERM BP-3758) possessed by Meiji Institute of Health Science of Meiji Milk Products Coo, Ltd., which has a length of about 7.9 kbp, which has a restriction endonuclease map as shown in FIG. 1, and which does not have recognition sites for BamHI, EcoRI, KpnI, PstI and SalI, the base sequence of the SmaI fragment with 1344 bp being represented as the Sequence Number 1 of the Sequence Table in Table 1 below. They named the plasmid pBUL1.

TABLE 1

(SEQ ID NO: 1)
Sequence Table:
Sequence Number: 1
Length of Sequence: 1344
Type of Sequence: Nucleic Acid
Number of Strand: Double-stranded
Topology: Linear
Kind of Sequence: Other Nucleic Acid
Origin:
Name of Microorganism: *Lactobacillus delbrueckii* subsp. *bulgaricus*
Name of Strain: M-878
Sequence:

| | | | | | | |
|---|---|---|---|---|---|---|
| CCCGGGGCGA | AACGACATGG | GGCGCTCAAA | CCATTGCTGA | GGCGATCAAT | TACGTGCAAG | 80 |
| CCCAGCATCC | CGATCACGGC | TATTTCCCAG | CTCGCCAAAA | TTCCGGCATG | AGGGTTGTTG | 120 |
| AACCGGGTGA | AAGAGCCACA | GGCGAAACGC | TTAGAATTAC | GATTGACGGA | CAGGAAAGAG | 180 |
| AATTTCCGTT | CAACGGCTTT | TTCTATAACC | GGGATTATGA | AATGACCGAG | GTTGGGTTTG | 240 |
| CTAACAGGTT | TGCCGATTGG | TACGCCAAAG | GGAAACTTGT | TTATCACCCC | GGCTTAAAGG | 300 |
| CGTGGCTTAT | GTACAACCCA | GAAACGGGGT | CATGGATGCC | GAATGAAGAC | GACAGACTGG | 350 |
| GCAAGGATTT | TAACCAGACC | CCGGAAAAAC | TCATCGATAA | CTTGCGGATA | AACCTCAAAT | 420 |
| TTGAACAACC | GCTATGGAAA | AAAGTTGGGT | TTAATCCCCA | AAAGCCTAAT | AATCAAACAT | 480 |
| TCGGGGAAAA | GGCTTATGCT | AGTGGCTATA | GCCGGATCAG | CACGGCCGCT | GGGCAAAAGG | 540 |
| CGACCCTTGA | ATTAGCTCAG | AGCCGTTTAA | CCGTGCGTGC | ATTTAACGAC | TGTAAGACCG | 600 |
| CGGCGAAACT | TTTTGACAAG | GTCACGGATG | CTGGTTTGCC | TAATAAAGCC | ACAGAGGGTG | 720 |
| ATGGCGGCAA | GCTCTGGGAT | CGTTTCCTGA | AAGAGACCTT | TTGCGGCGAT | CTTGATTTGA | 780 |
| TCGAGTTCGT | ACAGGCCTGC | ATAGGCTACA | GCATTACGGG | CAAAATCAAT | GAACAGGTCA | 840 |
| TGTTTATCTG | CAAAGGCAGT | GGGGGCAACG | GGAAGAGCAT | TTTTCTTGAA | TGCTTAAACG | 900 |
| AGGTGCTGGG | CGATTATAGC | TCTGTTATCC | CAATAGAAAC | GCTAACAGAC | AACGGCAAGG | 960 |

TABLE 1-continued (SEQ ID NO: 1)
Sequence Table:
Sequence Number: 1
Length of Sequence: 1344
Type of Sequence: Nucleic Acid
Number of Strand: Double-stranded
Topology: Linear
Kind of Sequence: Other Nucleic Acid
Origin:
Name of Microorganism: *Lactobacillus delbrueckii*
subsp. *bulgaricus*
Name of Strain: M-878
Sequence:

| CTCAGCGTGA | CGGATCAGCA | CCAAGTCCAG | ACCTTGCAAG | CCTTGAGGGC | AAGCGGTTCG | 1020 |
| TTATTACGAG | CGAACCGAAA | GAGCAGGTTA | CAATCGATGC | TGGGACGGTC | AAAACGGTGA | 1080 |
| CGGGTGGCAC | TAAGTTAAAA | GTTAGAATGC | TACACCAAAA | CCCGATTGAG | TTCCTGCCAC | 1140 |
| AGTTTAAAAT | TTGGTGGCAA | TCTAACGGCT | TGCCAAACGT | CAACTTTAAC | GATTATGCTA | 1200 |
| TTTTACGGCG | CTTGATCGTC | ATCCCGTTTA | AAAATGAGGT | GCGAGAGGAT | GCGGTAGATA | 1250 |
| TCAACCTCAA | AAGCAAGCTA | ATGAAAGAGA | AAGAGTTTAT | TTTAAAGTGG | TGTGTTGAGG | 1320 |
| GCGTGGCTAA | ATGGCAAGCC | CGGG | | | | 1344 |

Figure 1:
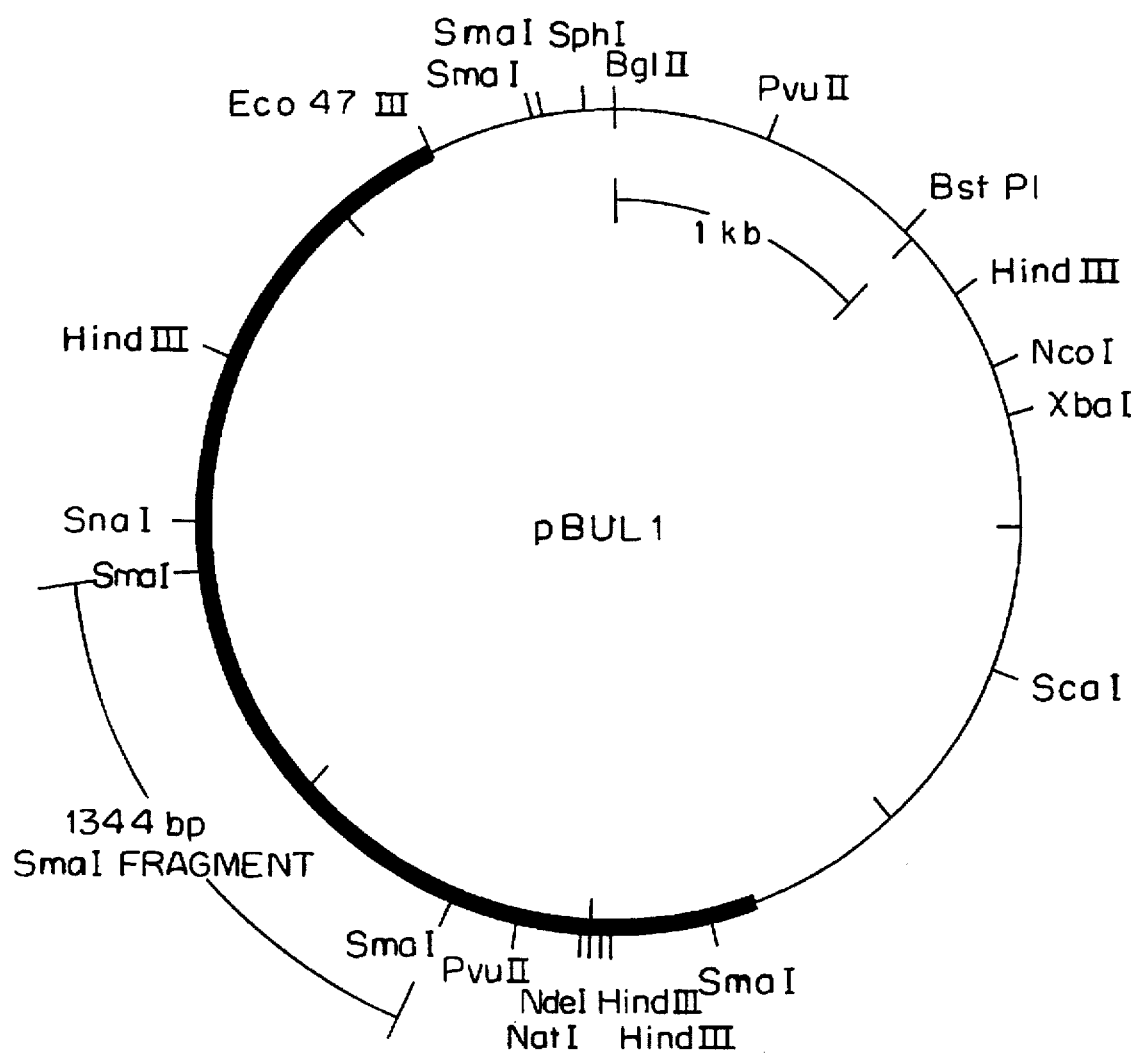
FIG. 1.

This is a restriction endonuclease map of pBUL1. The recognition site of each restriction enzyme is expressed by kbp unit, on the basis of BglII. pBUL1 does not have recognition sites for BamHI, EcoRI, KpnI, PstI and SalI. In the structure of pBUL1, the region necessary for replication of pBUL1 is shown by the thick line; and the region corresponding to the base sequence of the Sequence Number 1 (the third largest fragment of all SmaI fragments) is designated as "1344 bp SmaI fragment" in the outer periphery of the map.

FIG. 2:

This shows a scheme of construction of the erythromycin-resistance cassette plasmid p8Em1, in which Δ indicates the pUC118-derived multiple cloning site.

FIG. 3A–3D:

This shows restriction endonuclease maps of the derivatives of pBUL1, i.e., pX3, pX4, pS3 and pS4 (Although all of these plasmids are circular, they are represented as linear profiles on the basis of BglII.). In the drawing, the fine lines each indicate the sequence of pBUL1, and the thick lines each indicate the pAMβ1-derived erythromycin-resistance gene.

FIG. 4A–4B:

This shows restriction endonuclease maps of plasmids pU8ST8 and pU8ST9. In the drawing, the striped arrows each indicate the L-lactate dehydrogenase gene of *Streptococcus salivarius* subsp. thermophilus M-192 strain (ST-LDH gene); and the fine lines each indicate the sequence of plasmid pUC118. bla indicates the ampicillin-resistance gene.

FIG. 5:

This shows restriction endonuclease maps of plasmids pXL38, pXL39, pXL48 and pXL49 (Although all of these plasmids are circular, they are represented as linear profiles on the basis of BglII.). In the drawing, the fine lines each indicate the sequence of pBUL1, the thick lines each indicate the pAMβ1-derived erythromycin-resistance gene, and the striped arrows each indicate ST-LDH gene.

FIG. 6:

This shows a scheme to locate the region required for replication of pBUL1 by the deletion method.

FIG. 7:

This shows a restriction endonuclease map of pBR3Δ18E1 plasmid by ligation of pX3Δ18E plasmid with the *E. coli* plasmid (pBR322). In the drawing, the fine line indicates the sequence derived from plasmid pBR322, the thick line indicates the sequence derived from pX3Δ18E, the arrow (Em$^r$) indicates the erythromycin-resistance gene, and the arrow (Ap$^r$) indicates the ampicillin-resistance gene.

Figure 7:
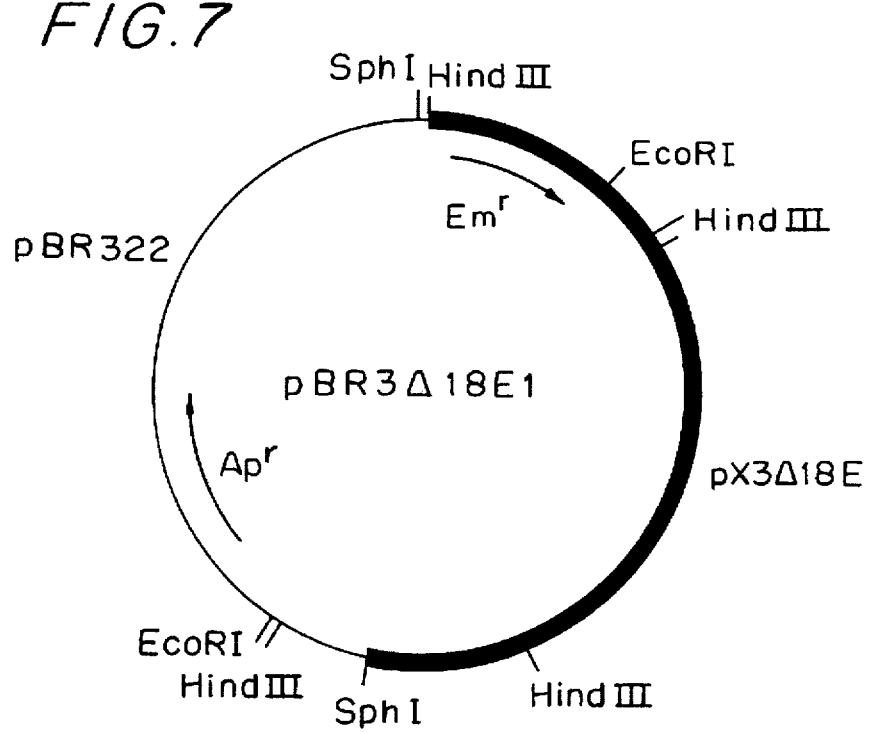
Figure 8:
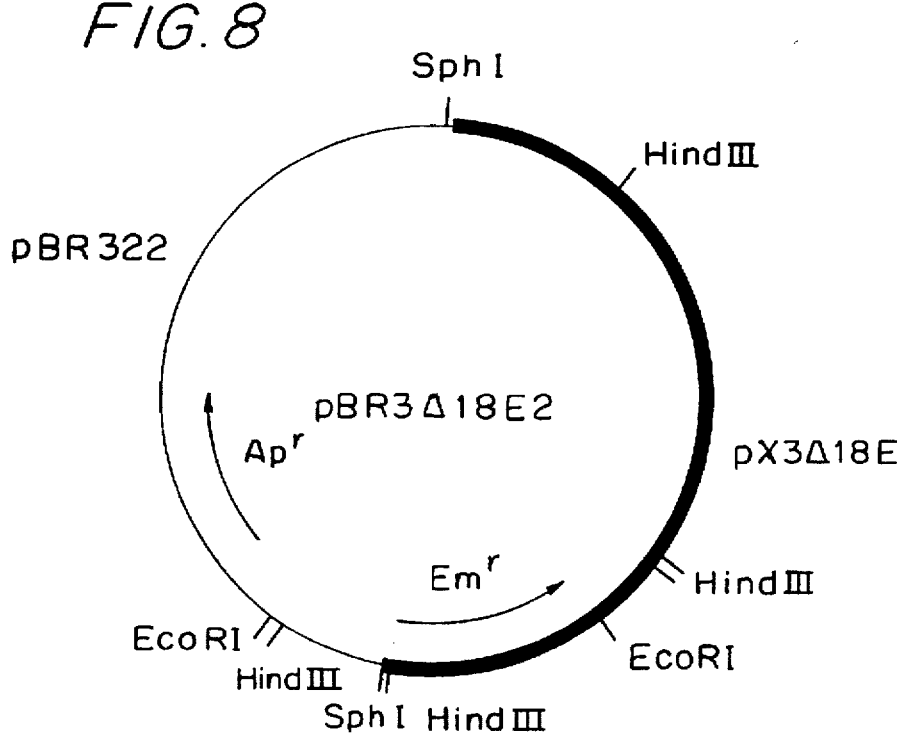

FIG. 8:

This shows a restriction endonuclease map of pBR3Δ18E2 plasmid. The symbols are the same as those, shown in FIG. 7.

FIG. 9:

This shows a restriction endonuclease map of p8X3Δ18E1 plasmid by ligation of pX3Δ18E plasmid with the *E. coli* plasmid (pUC118). in the drawing, the fine line indicates the sequence derived from plasmid pUC118, the thick line indicates the sequence derived from pX3Δ18E, the arrow (Em$^r$) indicates the erythromycin-resistance gene, and the arrow (Ap$^r$) indicates the ampicillin-resistance gene.

Figure 9:
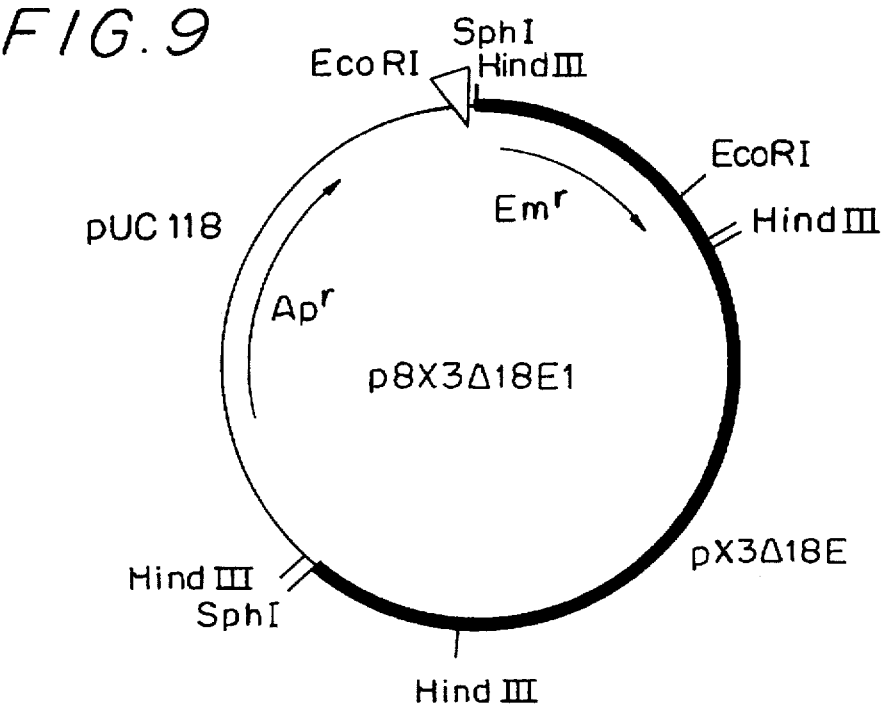
Figure 10:
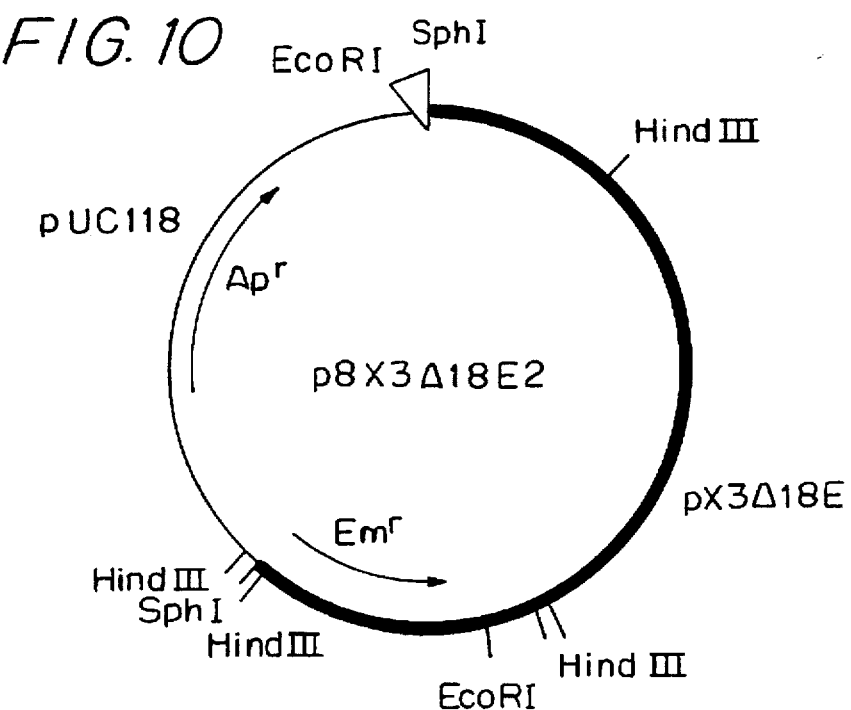

FIG. 10:

This shows a restriction endonuclease map of p8X3Δ18E2 plasmid. The symbols are the same as those shown in FIG. 9.

Since the phenotype encoded by the pBUL1 was cryptic, an erythromycin-resistance gene was added to the plasmid as a selective marker in transformation experiments (Erythromycin may be referred to simply as "Em" hereunder.). As a result, the present inventors have succeeded in obtaining transformants expressing the above-mentioned selective marker in microorganisms of three genera, namely *Bacillus subtilis*, *Lactococcus lactis* subsp. lactis and *Lactobacillus delbrueckii* subsp. lactis. The fact indicates that the plasmid pBUL1 (hereinafter often referred to as "the plasmid of the invention") has a broad host range in Gram-positive bacteria. The present invention has been completed on the basis of these findings.

Since the gene which participates in self-replicatability of pBUL1 is considered to be encoded in a part of the plasmid DNA of the present invention as reported in other plasmids, any other plasmid derivatives derived either by deletion of unnecessary regions for replication from the plasmid of the invention, or by insertion or addition of any other DNA to pBUL1 are also considered to have the same function as the plasmid of the invention. For instance, as described in Example 6 followed hereinafter, any plasmid causes no hindrance in replication, if it contains, as a region necessary for replication, a region necessary for replication in about 4 kbp DNA fragment indicated by the thick line in FIG. 1 between the recognition site for Eco47III and the position about 1.1 kbp apart clockwise from the ScsI site, namely about 0.45 kbp apart counterclockwise from the NdeI site. Therefore, the present invention is not restricted to only the plasmid pBUL1 itself but includes other derivative plasmids as obtained by modifying pBUL1 as well as other recombinant plasmids as obtained by inserting other gene(s), for example, marker(s) such as Em-resistance gene or exogeneous gene(s) such as L-lactate dehydrogenase gene, or other promoter(s) or operator(s) into it.

Figure 6:
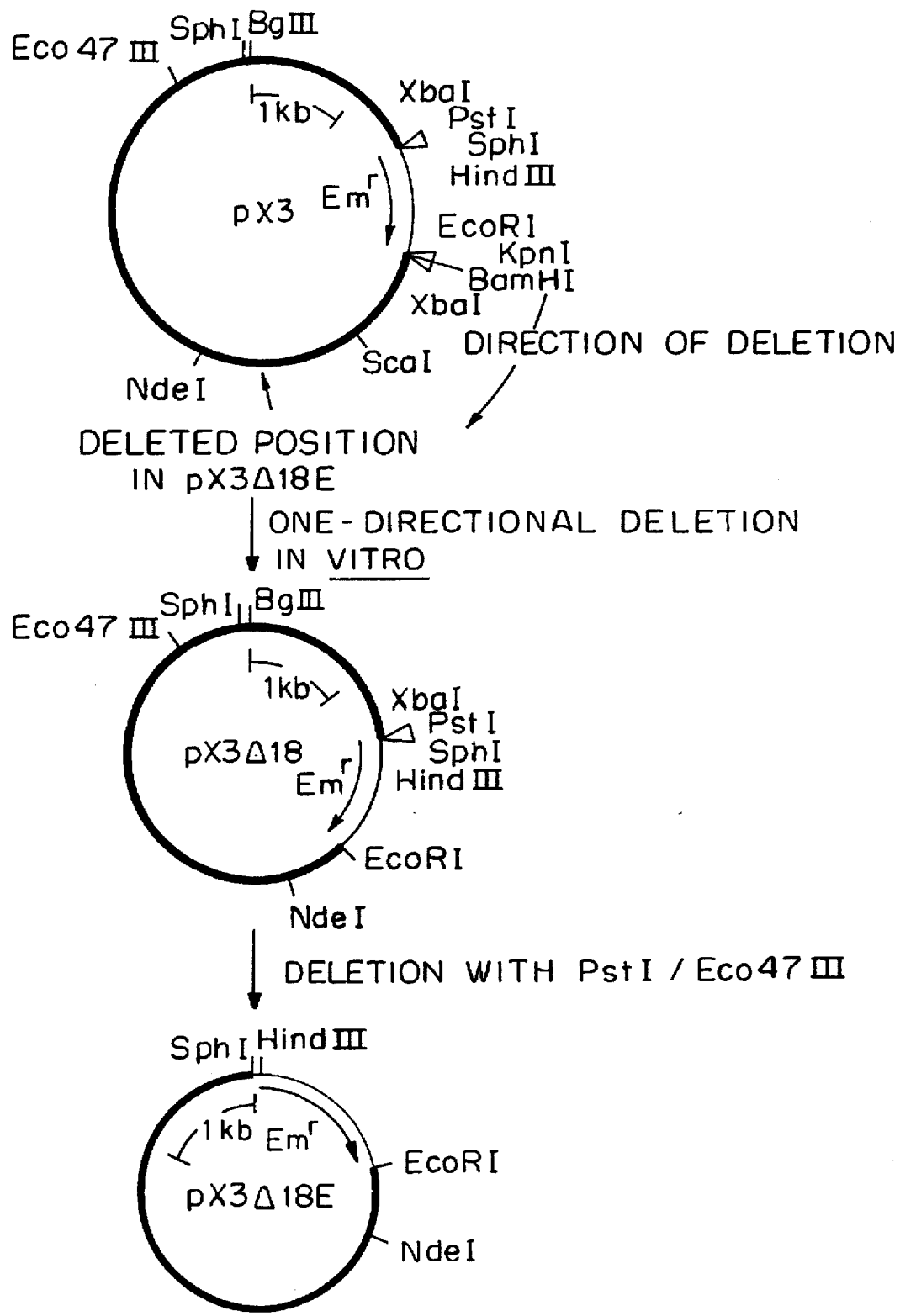

As derivative plasmids of pBUL1 of the present invention, for example, there are mentioned plasmids containing necessary regions for replication in the region of about 4 kbp shown as the thick line in FIG. 1 as mentioned above. As one example of them, there is the mentioned plasmid pX3Δ18E (FIG. 6, the bottom). This plasmid can be replicated not only in Gram-positive bacteria such as lactic acid bacteria but also in E. coli, as is obvious from Example 8. This plasmid itself is nothing but a plasmid with a broad-host-range, which has been desired in this technical field. Since this plasmid is one which can be replicated not only in Gram-positive bacteria (e.g., lactic acid bacteria, Bacillus subtilis) but also in Gram-negative bacteria (e.g., E. coli), it is effective as a novel versatile shuttle vector which has extremely high applicability and can be used in both Gram-positive bacteria and Gram-negative bacteria.

Another example of the pBUL1-derived plasmids can be obtained by ligation of other plasmids (fragments) with the region of pBUL1 necessary for replication, involved in the region of about 4 kbp shown as the thick line area in FIG. 1, or a DNA fragment of pBUL1 which contains this region. As the other plasmids to be ligated, various plasmids may be used widely. As some examples of them, there are exemplified E. coli-derived plasmids such as pBR series plasmids and pUC series plasmids.

Also the thus ligated plasmids have been identified to be replicable in both lactic acid bacteria and E. coli, like the above-mentioned plasmid pX3Δ18E, and they may also be used as plasmids with a broad-host-range which have heretofore been strongly desired in this technical field or as shuttle vectors between Gram-positive bacteria and Gram-negative bacteria. As examples of such ligated plasmids, there are exemplified pBR3Δ18E1, pBR3Δ18E2, p8X3Δ18E1, p8X3Δ18E2 (FIGS. 7 to 10), etc.

As mentioned above, plasmid pBUL1 and its derivative plasmids show a broad-host-range and are useful. Using them as a vector, expression of heterogeneous genes in lactic acid bacteria is possible.

For instance, where a recombinant plasmid was constructed by ligation of pBUL1 plasmid with an erythromycin-resistance gene as a selective marker gene and an L-lactate dehydrogenase gene derived from a yogurt lactococcus (Streptococcus salivarius subsp. thermophilus); (e.g., pXL38 in FIG. 5) as an exogenous gene, and the recombinant plasmid was introduced into Lb. lactis which does not naturally have L-lactic acid producibility, the resulting erythromycin-resistance transformant produced not only D-lactic acid but also almost the same amount of L-lactic acid as metabolic end-products.

Thus, plasmid pBUL1 and its derivative plasmids are useful also as a vector for expression of heterogeneous genes in lactic acid bacteria.

For preparing the plasmid pBUL1 of the present invention, Lb. bulgaricus M-878 strain is first cultivated in a liquid medium which is used for cultivation of lactic acid bacteria, for example, LCM medium (reference 8), according to ordinary methods of cultivating lactic acid bacteria under ordinary incubation conditions. Next, the incubated cells are collected and are then subjected to lysis by known methods for lactic acid bacteria, for example, by using an enzyme such as lysozyme or mutanolysin, etc. From the resulting cell lysate, the intended plasmid can be isolated and purified by a conventional emplyed method, such as phenol extraction and cesium chloride density gradient centrifugation in the presence of ethidium bromide. For construction of the derivative plasmids of pBUL1, which are other plasmids of the present invention, the plasmid pBUL1 may be treated for digestion, ligation and others by known methods (reference 10).

In order to transform microorganisms by introducing thereinto a recombinant plasmid as obtained by inserting a selective marker gene to the plasmid pBUL1, a known method which is considered to be the best for the host may be selected from conventional methods, such as calcium chloride method, protoplast-polyethylene glycol method, electropotation method, etc., with no particular limitation, according to the characteristics of microorganisms to be transformed. Where lactic acid bacteria are used as a host, the electropotation method is preferred. A marker for selecting the transformants may be selected from various antibiotic-resistance genes known in this technical field. Where the transformed microorganisms are intended to be used in producing foods or medicines, use of markers which have been confirmed to be safe is desirable. If desired, other base sequences participating in control of expression, such as promoters, may also be inserted into the plasmids of the invention.

Recombinant plasmids are considered to be safe which are constructed from pBUL1 plasmid or its derivative, an enzyme gene derived from a microorganism used in food production and a safe selective marker gene. Therefore, the transformants of food-producing bacteria such as lactic acid bacteria with such a safe plasmid are also considered to be safe. Such safe transformants may be incubated by ordinary methods to produce a large amount of enzymes and physiologically active substances, and they may be used in various food productions in ordinary ways to attain the intended objects. In addition, since the safety of the transformants is highly assured in any case, they do not cause by-production of any biohazards or harmful substances. Accordingly, it is expected that they could advantageously be utilized in industrial production of medicines and foods which especially need safe methods of production.

Next the present invention will be explained hereunder by way of the following examples.

EXAMPLE 1

(Preparation of Plasmid pBUL1)

Lactobacillus delbrueckii subsp. bulgaricus M-878 strain (FERM BP-3758, as possessed by Meiji Institute of Health Science; herein often referred to simply as M-878 strain) was subcultivated with a skim milk medium (liquid medium as prepared by dissolving 10% skim milk powder and 0.1% yeast extract in distilled water and sterilized at 121° C. for 7 minutes) and inoculated (0.5%) in 6 liters of LCMG medium (as prepared by adding 1% (w/v) glucose to LCM medium) and incubated at 37° C. for 15 hours.

After the incubation, the cells were Collected by centrifugation and washed twice with 20 mM Tris-HCl buffer (pH 7.0). The washed cells were suspended in 480 ml of a hypertonic buffer (20 mM Tris buffer containing 0.3M raffinose, 5 mM magnesium chloride and 5 mM calcium chloride; pH 7.0). To this were added mutanolysin and lysozyme in an amount of 5 μg/ml and 500 μg/ml, respectively, as the final concentrations, and were incubated at 37° C. for 10 minutes. Then, 54 ml of 250 mM EDTA (pH 8.0) was added to the resulting solution, which was then subjected to centrifugation to collect the precipitates.

The precipitates were then suspended in 240 ml of 50 mM Tris buffer (pH 8.0) containing 6.7% (w/v) sucrose and 25 mM EDTA. The resulting suspension was then processed according to Anderson & Mckay method (reference 9), from lysis with SDS to rough purification of plasmid DNA.

The crude plasmid DNA preparation thus obtained was subjected to RNase treatment by an ordinary method (reference 10) and then to cesium chloride density gradient centrifugation in the presence of ethidium bromide to obtain about 1 μg of purified pBUL1 plasmid DNA.

The pBUL1 plasmid was cut with various commercially available restriction enzymes, and the length of each fragment obtained was calculated after agarose gel electrophoresis. As a result, pBUL1 was identified to be a circular double-stranded DNA plasmid having the restriction endonuclease map in FIG. 1 with a total length of about 7.9 kbp. pBUL1 did not have recognition sites for BamHI, EcoRI, KpnI, PstI and SalI. Of five fragments obtained by digestion of pBUL1 with SmaI, the third largest fragment (1344 bp; the position of which has been designated in the outer periphery of the restriction endonuclease map in FIG. 1 as "1344 bp SmaI fragment") was analyzed with respect to the base sequence thereof, which is shown as Sequence Number 1 in Table 1.

EXAMPLE 2

(Addition of Selective Marker Em-resistance Gene to pBDL1)

Figure 2:
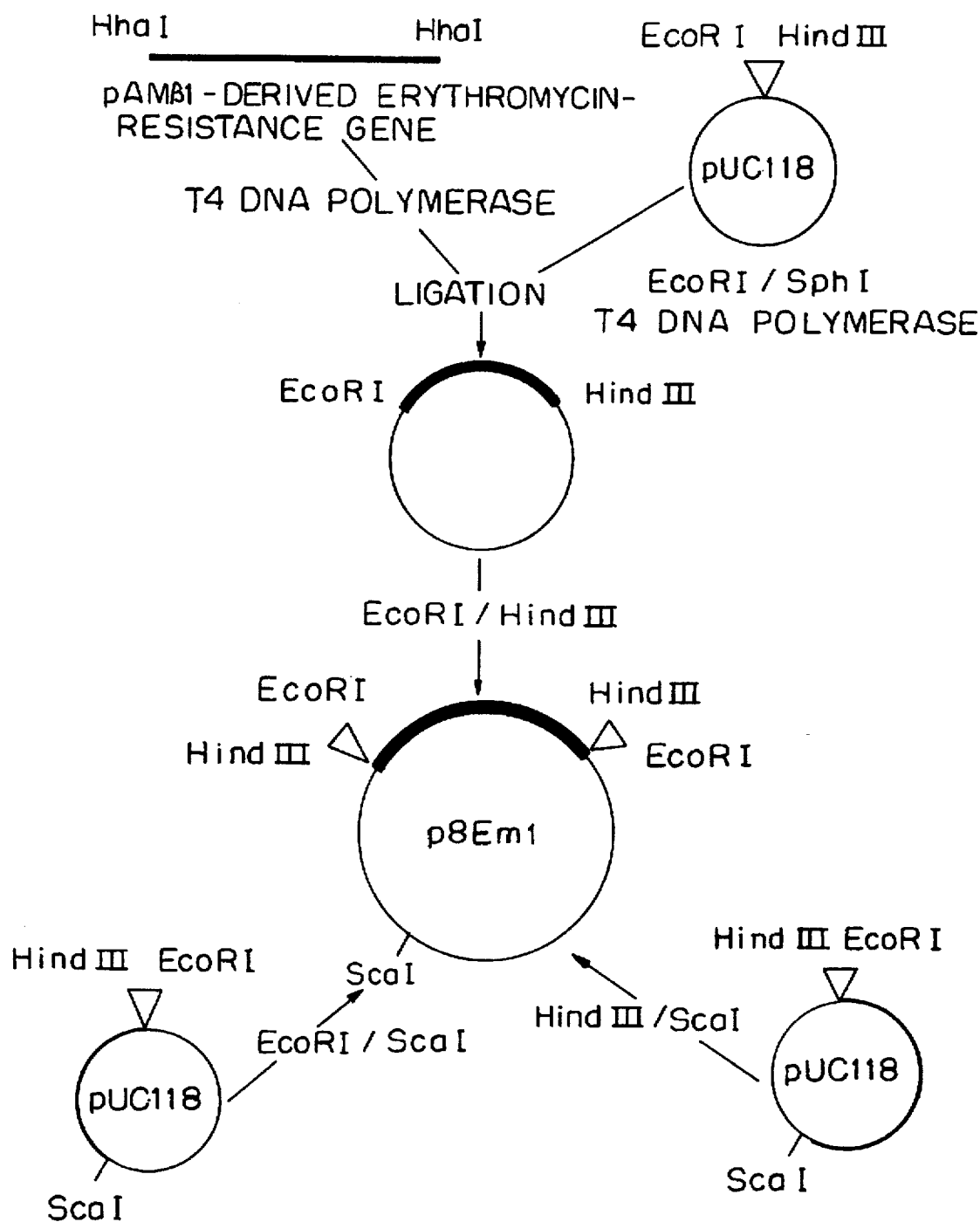

First, conjugatively transmissible plasmid pAM β1 ( reference 11) derived from *Enterococcus faecalis* was cut with HhaI and subjected to agarose gel electrophoresis to thereby cut out a gel fraction containing DNA fragments ranging about 1.1 kbp having the Era-resistance gene. DNAs were isolated from the thus cut-out gel using a GENECLEAN DNA purifying kit (product by BIO101 Co.). The DNA fragment was ligated to *E. coli*-derived pUC118 plasmid (product by Takara Shuzo Co.) according to the process shown in FIG. 2 to prepare "cassette plasmid" p8Em1 in order to excise the Em-resistance gene successfully with various restriction enzymes.

Next, about 0.25 μg of p8Em1 DNA was cut with XbaI and was ligated with a fragment as obtained by cutting about 0.025 μg of pBUL1 DNA with XbaI. A half of the reaction mixture after the ligation was used in transformation of *Bacillus subtills* 207-25 strain (reference 13) by the method of Chang et al (reference 12). One third of the transformed cells were spread on a plate of DM3 medium containing 25 μg/ml of erythromycin and incubated for 2 days at 37° C. to obtain Em-resistant transformants.

Plasmid DNAs were prepared from the transformants obtained, and the restriction endonuclease cleavage pattern of the plasmids was analyzed. When pBUL1 and the Em-resistance gene were ligated at XbaI site, five transformants of all the nine analyzed contained a plasmid having the restriction endonuclease map of A in FIG. 3; and two of them contained a plasmid having the restriction endonuclease map of B in FIG. 3. The plasmid with the map A is FIG. 3 was named pX3; and that with the map B in the same was named pX4.

In the same manner as above, except that p8Em1 was cut with SmaI and pBUL1 was cut with ScaI, and the resulting fragments were subjected to blunt end ligation followed by transformation of *Bacillus subtilis* 207-25 strain with the ligated products, Em-resistant transformants were also obtained. Five of the six transformants, analyzed with respect to plasmids therein, contained a plasmid having the restriction endonuclease map of C in FIG. 3; and one of them contained a plasmid having the restriction endonuclease map of D in FIG. 3. These plasmids were named pS3 and pS4, respectively.

As mentioned above, recombinant plasmids pX3, pX4, pS3 and pS4 (all having a length of about 9.0 kbp) were constructed by introducing the pAMβ1-derived Em-resistance gene (having a length of about 1.1 kb) to pBUL1. In addition, it was shown that pBUL1 could function as a plasmid replicon in *Bacillus subtilis*.

EXAMPLE 3

(Transformation of *Lactococcus lactis* subsp. lactis):

*Lactococcus lactis* subsp. lactis (hereinafter often referred to simply as "*Lc. lactis*") IL1403 strain (as obtained from Dr. Alain Chopin, INRA, France) was used. To this was introduced pBUL1 having the Em-resistance gene, whereby a transformant of *Lc. lactis* showing Em-resistance was successfully obtained. The details are mentioned below.

From the transformants of *Bacillus subtills* obtained in Example 2, the recombinant plasmids, PX3 and pX4, constructed by inserting the Em-resistance gene into pBUL1 were prepared by the method of reference 14.

Next, pX3 and pX4 each were introduced into *Lc. lactis* IL1403 strain according to the method of reference 1. The transformants were obtained by selecting on agar plates of BL medium (product by Eiken Chemical Co.) containing 25 μg/ml of Em.

The transformants were incubated in LCMG medium, and plasmids were obtained from the cells after Anderson et al. (reference 9). The plasmids thus obtained were shown to have the same restriction enzyme recognizing sites as those of the plasmids used for the transformation. From the result, it was concluded that pBUL1 also functioned as a plasmid replicon in not only *Bacillus subtills* but also *Lc. lactis*.

EXAMPLE 4

(Transformation of *Lactobacillus delbrueckii* subsp. lactis):

From the transformants of *Lactococcus lactis* subsp. lactis IL1403 obtained in Example 3, plasmids pX3 and pX4 were prepared. Using them, *Lb. lactis* ATCC 12315 strain and M-908 strain, possessed by Meiji Institute of Health Science, were transformed by electroporation. There was no report of success in transformation of *Lactobacillus delbrueckii* species being commercially useful, despite studies by many researchers. Using the plasmid the invention, transformation of *Lb. lactis* was attained for the first time, as mentioned below.

*Lb. lactis* ATCC 12315 strain or N-908 strain as subcultivated in a skim milk medium was inoculated in LCMG medium in a concentration of 2% and incubated for 2 hours at 42° C. The cells were collected and washed, and then suspended in EP buffer (containing 0.4M sucrose, 1 ml magnesium chloride and 7 ml potassium dihydrogenphosphate; pH 7.4) at a concentration of $OD_{660}$=4.0 and cooled on ice. 0.8 ml of the cell suspension was put in an electroporation cuvette, about 0.1 to 2 μg of pX3 or pX4 plasmid was added thereto, and an electric pulse of 25 μF at 2.5 kV was discharged thereto with Gene Pulser (manufactured by Bio-Rad Co.).

Immediately after the discharge, the cells were suspended in 4 ml of an expression medium (LCMG medium to which 0.2M raffinose, 5 mM magnesium chloride and 1% lactose had been added) and incubated statically for 2.5 hours at 37° C. All the culture liquid thus incubated was poured into several plates and 10 to 15 ml of BL agar medium (sterilized and kept at 50° C.) containing 25 μg/ml of Em was added thereto and mixed. After the culture medium solidified, the plates were incubated anaerobically in Gaspak system (manufactured by Beckton-Dickinson Co.) at 37° C. for 2 to 4 days, and the transformants were selected. According to the method, about 10 to 100 transformants per μg of the plasmid DNA were obtained.

The Em-resistant clones thus obtained showed a strong Em-resistance (>1 mg Em/ml) and had a plasmid having the same restriction endonuculease map as pX3 or pX4. From these results, they were confirmed to be transformants. Further, using the pX3 or pX4 plasmid DNA obtained from the transformants, the transformation frequency in *Lb. lactis* ATCC 12315 strain increased by about 10 times.

No transformants of *Lb. lactis* have heretofore been obtained by using other plasmids such as pGK12 or IL253 under the same conditions as above. From the fact, it is obvious that the pBUL1 of the present invention is useful as a vector for *Lb. lactis*.

EXAMPLE 5

Figure 4A:
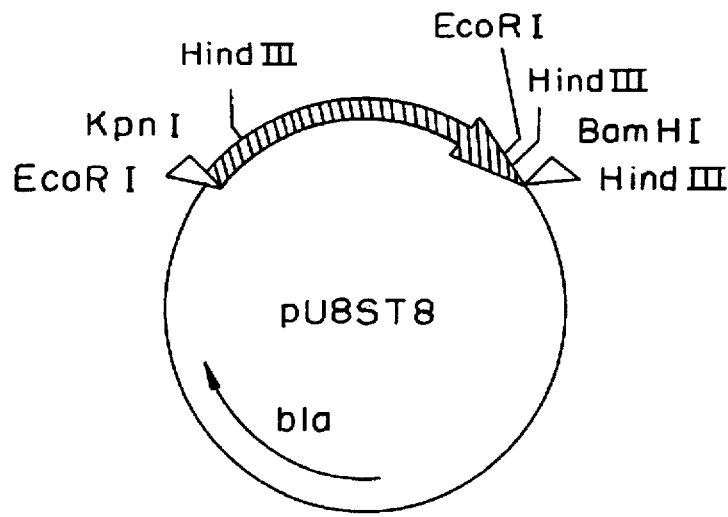
Figure 4B:
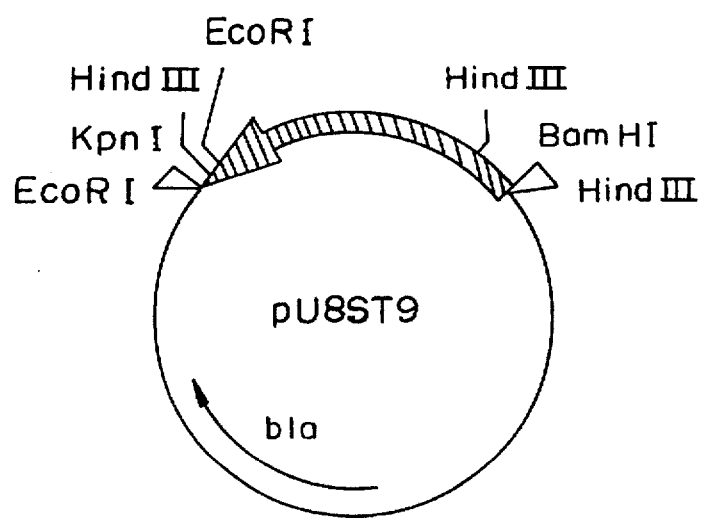

(Introduction and Expression in *Lb. lactis* of L-lactate Dehydrogenase Gene inserted in pBUL1):

A restriction enzyme SspI fragment (about 1.2 kbp) containing a gene (Japanese Patent Application No. 2-45976) coding for L-lactate dehydrogenase (hereinafter referred to as "ST-LDH") derived from a lactic acid bacterium *Streptococcus salivarius* subsp. thermophilus M-192 strain (possessed by Meiji Institute of Health Science) was inserted into the SmaI recognition site of pUC118, to construct the recombinant plasmids pU8ST8 and pU8ST9 as shown in FIG. 4-A and FIG. 4-B, respectively.

These recombinant plasmids were cut with BamHI and KpnI and subjected to agarose gel electrophoresis. About 0.02 μg of DNA fragments containing the ST-LDH gene was cut out and isolated using a GENECLEAN DNA purification kit (manufactured by BI0101 Co.). These DNA fragments were ligated with about 0.3 μg of pX3 or pX4, obtained in Example 2, cut with BamHI and KpnI. Using this ligation mixture, *Lc. lactis* IL1403 strain was transformed, whereby transformants having the plasmids as shown in FIG. 5 were obtained. These plasmids were named pXL38, pXL39, pXL48 and pXL49, respectively. These plasmids were prepared by the method of reference 9 and were used for transformation of *Lactobacillus delbrueckii* subsp. lactis ATCC 12315 strain by the same method as shown in Example 4. As a result, Em-resistant transformants were obtained. These carried plasmids each having the same restriction endonuclease map as the introduced plasmids.

These transformants were incubated in a skim milk medium. The culture was diluted with distilled water and subjected to centrifugation. The lactic acid in the resulting supernatant was measured by the use of a lactic acid measuring kit (F Kit L-lactic Acid; manufactured by Boehringer Mannheir). As a result, L-lactic acid, which is not naturally produced at all by the host, was detected in an amount almost equivalent to D-lactic acid produced.

The cells of one of the transformants were disrupted and the cell extract was prepared. As a result, L-lactate dehydrogenase activity, which is not detected in the host cells, was detected in the cell extract of the transformant. The L-lactate dehydrogenase from the transformant was purified and the sequence of the 18 N-terminal amino acids thereof was examined. As a result, it was identical to that of ST-LDH. From the above-mentioned results, it was shown that a heterogeneous gene expression was possible in *Lb. lactis* with pBUL1 as a replicon.

EXAMPLE 6

(Presumption of the Region in pBUL1 necessary for Replication by a Deletion Method)

pX3 was cut with BamHI and KpnI and subjected to deletion in the direction as indicated in FIG. 6, by the use of a DNA deletion kit for kilosequencing (manufactured by Takara Shuzo Co.). Each reaction mixture was applied to transform *Lc. lactis* IL1403 in the same method as in Example 3, and the transformants were selected in the presence of 25 μg/ml of Em.

Plasmids harboured by the Em-resistant transformants were prepared and their restriction enzyme recognition sites were examined. As a result, the shortest deletant of pX6b 3was obtained whose deletion proceeded to the position in pX3 shown in FIG. 6, namely, the position about 1.1 kbp clockwise apart from ScaI site and about 0.45 kbp counter-clockwise apart from NdeI site. The deleted plasmid was named pX3Δ18 and it was further cut with both PstI and either of BglII, SphI and Eco47III and then subjected to self-circularizing ligation. The reaction mixture was used in transformation of *Lc. lactis* IL1403 strain and the selection of the transformants was performed as in Example 3. As a result, transformants having plasmids of various sizes were obtained. The plasmid pX3Δ18E as shown in FIG. 6 is the shortest one, which was formed by cutting pX3Δ18 with PstI and Eco47III followed by self-ligation. The region necessary for replication of pBUL1 was found to be contained in about 4 kbp DNA fragment of pX3Δ18E.

EXAMPLE 7

(Formation of Shuttle Vectors by Ligation of pX3Δ18E Plasmid with *E. coli* Plasmid)

pX3Δ18E plasmid obtained in Example 6 was prepared from *Lc. lactis* IL1403 strain by the method of reference 9. The thus obtained pX3Δ18E was cut with SphI in the multi-cloning site and was ligated with a DNA fragment obtained by cutting *E. coli* plasmid pBR322 (manufactured by Takara Shuzo Co. ) or pUC118 with SphI. The reaction mixture was used to transform *E. coli* TG1 strain [Δ(lac-pro) supE thi hsdD5/F' traD36 proA+B+lacI$^q$ lacZΔM15] (manufactured by Amersham Co.) by the well-known calcium chloride method. The transformants were selected with 500 μg Em/ml. They had a recombinant plasmid composed of pX3Δ18E and pBR322 or pUC118, as shown in FIG. 7 to FIG. 10 (pBR3Δ18E1, pBR3Δ18E2; p8X3×8E1, p8X3Δ18E2).

These transformants showed ampicillin resistance (50 μg/ml) derived from *E. coli* pBR322 and pUC118 plasmids. These recombinant plasmids isolated and purified from *E. coli* were used to transform *Lc. lactis* IL1403 strain and transformants were selected with 25 μg/ml of Em as shown in Example 3. As a result, Em-resistant transformants were obtained. The plasmids possessed by the transformants were prepared and the restriction enzyme-recognition sites were examined. As a result, they each had the same restriction endonuclease map as the map of those prepared from *E. coli*. From these results, pX3Δ18E, one of the derivatives of pBUL1, was found to be a useful shuttle vector if it is ligated with an *E. coli* plasmid. For the transformants with such a recombinant plasmid could be selected with ampicillin and Em, or Em when the host was either *E. coli* or lactic acid, respectively. Thus, the usefulness of pBUL1 was further proved.

EXAMPLE 8

(Replication of pX3Δ18E Plasmid in *E. coli*):

The plasmid pX3Δ18E, obtained in Example 6, was prepared from the transformant of *Lc. lactis* IL1403 by the method of reference 9, and was used to transform *E. coli* TG1 strain in the same manner as in Example 7. The thus obtained Em-resistant (Em 500 μg/ml) transformant had a plasmid having the same restriction endonuclease map as that of pX3Δ18E used for the transformation. From the fact, it was found that the pX3Δ18E plasmid, a derivative of pBUL1, is replicable even in *E. coli*, that *E. coli* with pX3Δ18E may be selected on the basis of the Em resistance and that pX3Δ18E is useful as a shuttle vector between Gram-positive bacteria and Gram-negative bacteria. Thus, the usefulness of pBUL1 was further proved.

References:
1. Holo, H. and I. F. Nes, (1989) Appl. Environ. Microbiol., 55 (12) 3119–3123.
2. Mercenier, A., (1990) FEMS Microbiol. Rev., 87, 61–77.
3. Scheirlinck, T., et al., (1989) Appl. Environ. Microbiol., 55 (9) 2130–2137.
4. Chassy, B. M. and J. L. Flickinger, (1987) FEMS Microbiol. Lett., (44) 173–177.
5. de Vos, W. N., (1987) FEMS Microbiol. Rev., 46, 281–295.
6. Kok, J. et al., (1984) Appl. Environ. Microbiol., 48, 726–731.
7. Simon, D. and A. Chopin, (1988) Biochimie, 70 (4) 559–566.
8. Efthymiou, C., et at., (1962) J. Infect. Dis., 110, 258–267.
9. Anderson, D. and L. L. Mckay, (1983) Appl. Environ. Microbiol., 46, 549–552.
10. Maniatis, T., et al., (1982) Molecular Cloning : A Laboratory Manual. Cold Spring Harbor Laboratory, Cold Spring Harbor, N.Y.
11. LeBlanc, D. J. and L. N. Lee, (1984) J. Bacteriol., 157, 445–453.
12. Chang, S. and S. N. Cohen, (1979) Mol. GeL. Genet., 168, 111–115.
13. Yamane, K., et al., (1984) J. Biochem., 96, 1849–1858.
14. Yamane, K. (1987) "Kosoh-kin (*Bacillus subtilis*)", in Biseibutsu-gaku Kiso Kohza (Lectures on Fundamental Microbiology) (Ando, T. and Sakaguchi, K. (eds.)), pp. 168–215 (1987)

Advantage of the Invention

The species *Lactobacillus delbrueckii* is an industrially useful lactic acid bacterium, including subsp. bulgaricus and subsp. lactis which are important in production of and cheese and subsp. delbrueckii which is important in production of lactic acid.

However, with respect to *Lactobacillus delbrueckii*, neither transformation nor the presence of an autonomously replicable plasmid has heretofore been reported. The plasmid of the present invention is the first reported up to now. Using the plasmid of the present invention as a replicon, transformation of *Lb. lactis*, which is one of this species, has become possible for the first time. Accordingly, it is expected that various genes are inserted into the plasmid of the present invention to give recombinant plasmids which are introduced into subspecies of *Lactobacillus delbrueckii* to construct improved strains having useful characteristics for example, a high lactose metablizing ability or an improved milk protein degrading activity. In addition, the present invention provides a plasmid with a broad-host-range shuttle vector. Thus, the effectiveness of the present invention is further elevated.

Since the plasmid of the invention is one isolated from a strain of *Lb. bulgaricus* existing in yogurt, its safety has been confirmed historically. In addition, since the plasmid of the invention can replicate not only in species of *Lactobacillus delbrueckii* but also in other bacteria important in the food industry, such as the genera Bacillus and Lactococcus, it is expected to be useful not only in the production of various foods but also in breeding of micro-organisms which produce various enzymes and physiologically active substances.

Reference to Deposited Microorganism under Rule 13-2:
1. *Lactobacillus delbrueckii* subsp. bulgaricus M-878
   a. Name and Address of the Institution for Deposition of the present Microorganism:
      Name: Fermentation Research Institute, Agency of Industrial Science and Technology, Ministry of International Trade and Industry
      Address: 1-3, Higashi 1-chome, Tsukuba-shi, ibaraki-ken, 305, Japan
   b. Date of Deposition in the Institution stated in a: Jan. 29, 1991
   c. Deposition Number rendered by the Institution stated in a: FERM BP-3758

---

We claim:

1. A *Lactobacillus delbrueckii* transformant which has been transformed with a recombinant plasmid comprising at least one foreign gene and a region necessary for replication of plasmid pBUL1, containing the SmaI fragment of 1344 bp shown in SEQ ID NO: 1.

2. The transformant according to claim 1 wherein the region necessary for replication is a DNA fragment shown by the thick line in FIG. 1, which is about 4 kbp between the position of the Eco47III site and the position about 1.1 kbp clockwise from the ScaI site and about 0.45 kbp counter-clockwise from the NdeI site.

3. The transformant according to claim 2 wherein said bacterial transformants belong to *Lactobacillus delbrueckii* subsp. delbrueckii.

4. The transformants according to claim 3 wherein the foreign gene is an L-lactate dehydrogenase gene.

5. The transformant according to claim 2 wherein said bacterial transformants belong to *Lactobacillus delbrueckii* subsp. bulgaricus.

6. The transformants according to claim 5 wherein the foreign gene is an L-lactate dehydrogenase gene.

7. The transformant according to claim 2 wherein said bacterial transformants belong to *Lactobacillus delbrueckii* subsp. lactis.

8. The transformant according to claim 7 wherein the foreign gene ms an L-lactate dehydrogenase gene.

9. The transformant according to claim 2 wherein the foreign gene is an L-lactate dehydrogenase gene.

10. The transformant according to claim 1 wherein said bacterial transformants belong to *Lactobacillus delbrueckii* subsp. delbrueckii.

11. The transformant according to claim 10 wherein the foreign gene is an L-lactate dehydrogenase gene.

12. The transformant according to claim 1 wherein said bacterial transformants belong to *Lactobacillus delbrueckii* subsp. bulgaricus.

13. The transformant according to claim 12 wherein the foreign gene is an L-lactate dehydrogenase gene.

14. The transformant according to claim 1 wherein said bacterial transformants belong to *Lactobacillus delbrueckii* subsp. lactis.

15. The at transformant according to claim 14 wherein the foreign gene is an L-lactate dehydrogenase gene.

16. The transformant according to claim 1 wherein the foreign gene is an L-lactate dehydrogenase gens.

* * * * *